United States Patent [19]

Sekii et al.

[11] Patent Number: 5,139,021

[45] Date of Patent: Aug. 18, 1992

[54] BIOLOGICAL INFORMATION MEASUREMENT APPARATUS

[75] Inventors: Shigekazu Sekii; Makoto Ikeda; Kouji Tsuchida, all of Fuji, Japan

[73] Assignee: Terumo Kabushiki Kaisha, Tokyo, Japan

[21] Appl. No.: 718,921

[22] PCT Filed: Mar. 3, 1988

[86] PCT No.: PCT/JP88/00235

§ 371 Date: Sep. 5, 1989

§ 102(e) Date: Sep. 5, 1989

[87] PCT Pub. No.: WO88/06424

PCT Pub. Date: Sep. 7, 1988

Related U.S. Application Data

[63] Continuation of Ser. No. 415,238, Sep. 5, 1989, abandoned.

[30] Foreign Application Priority Data

Mar. 5, 1987 [JP] Japan .................................. 62-48827
Mar. 5, 1987 [JP] Japan .................................. 62-48828
Mar. 5, 1987 [JP] Japan .................................. 62-48829
Mar. 5, 1987 [JP] Japan .................................. 62-48830

[51] Int. Cl.$^5$ .............................................. A61B 5/05
[52] U.S. Cl. .................................... 128/630; 128/713; 128/908
[58] Field of Search .......................... 128/713, 908, 630

[56] References Cited

U.S. PATENT DOCUMENTS

| | | | |
|---|---|---|---|
| 3,690,313 | 9/1972 | Weppner et al. | 128/908 |
| 3,808,502 | 4/1974 | Babilius | 128/908 |
| 3,886,932 | 6/1975 | Suessmilch | 128/908 |
| 3,910,257 | 10/1975 | Fletcher et al. | 128/908 |
| 4,245,650 | 1/1981 | Welker et al. | 128/908 |
| 4,741,334 | 5/1988 | Irnich | 128/908 |

*Primary Examiner*—William E. Kamm
*Attorney, Agent, or Firm*—Staas & Halsey

[57] ABSTRACT

A biological information measurement apparatus for measuring biological information by contacting a probe with a living body or inserting the probe into the living body includes a biological information detecting circuit for electrically detecting biological information, and a biological information processing circuit for digitally processing the biological information detected. Exchange of signals between the biological information detecting circuit and biological information processing circuit is performed in an electrically isolated state. Preferably, the apparatus is equipped with a first power supply circuit for supplying power solely to the biological information detecting circuit, and a second power supply circuit for supplying power to the first power supply circuit, wherein supply of power from the second power supply circuit to the first power supply circuit is performed in an electrically isolated state. Preferably, whether or not a leakage current is present in the living body is detected by detecting and comparing the amount of electrical bias applied to a sensing element in the probe and an amount of electrical bias fed back via the sensing element. Preferably, whether or not the probe is connected and the type of probe are determined before measurement of biological information by reading the quantity of electricity of an element for correcting the electrical characteristics of the sensing element in the probe.

3 Claims, 9 Drawing Sheets

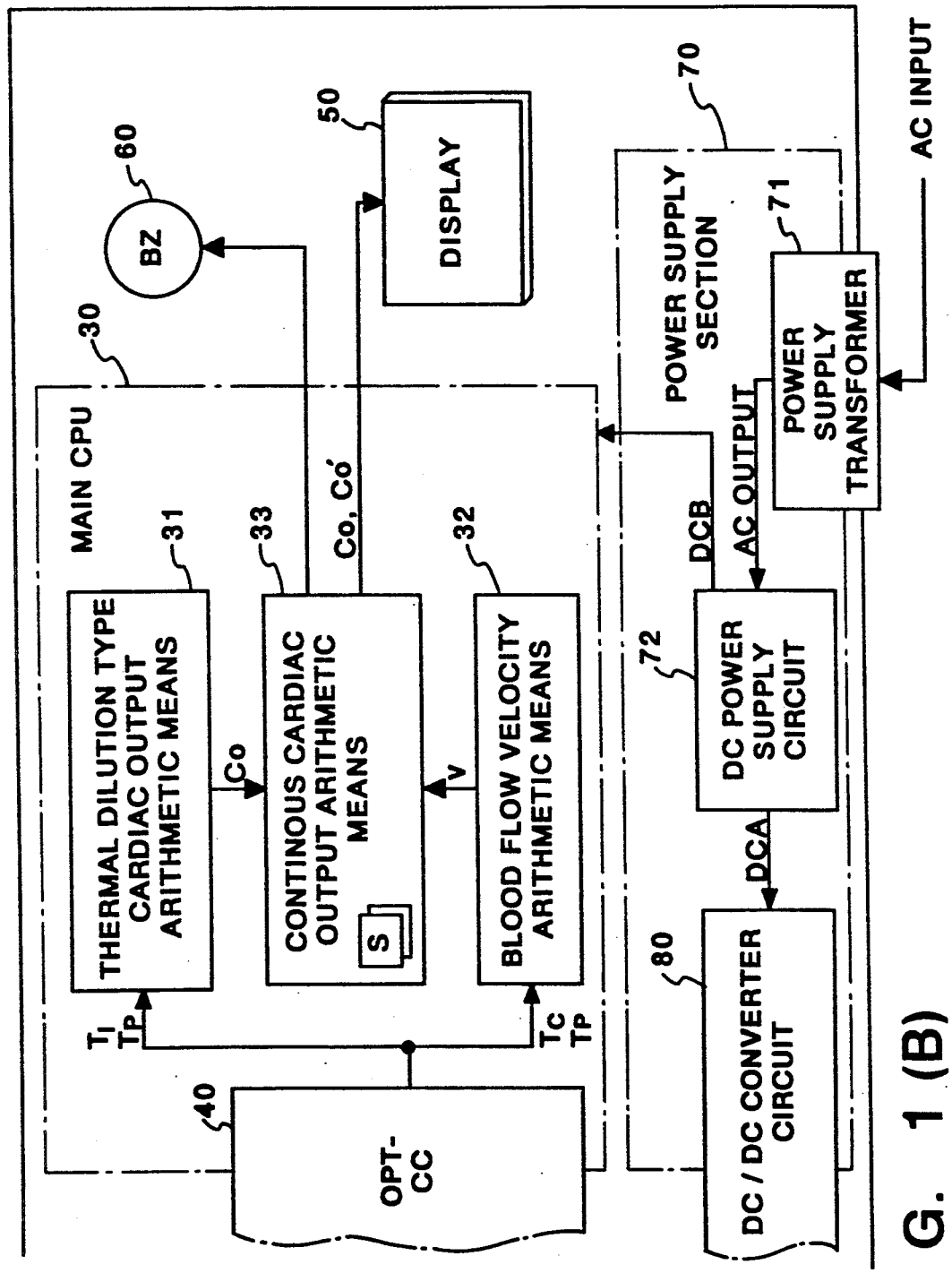
F I G. 1 (B)

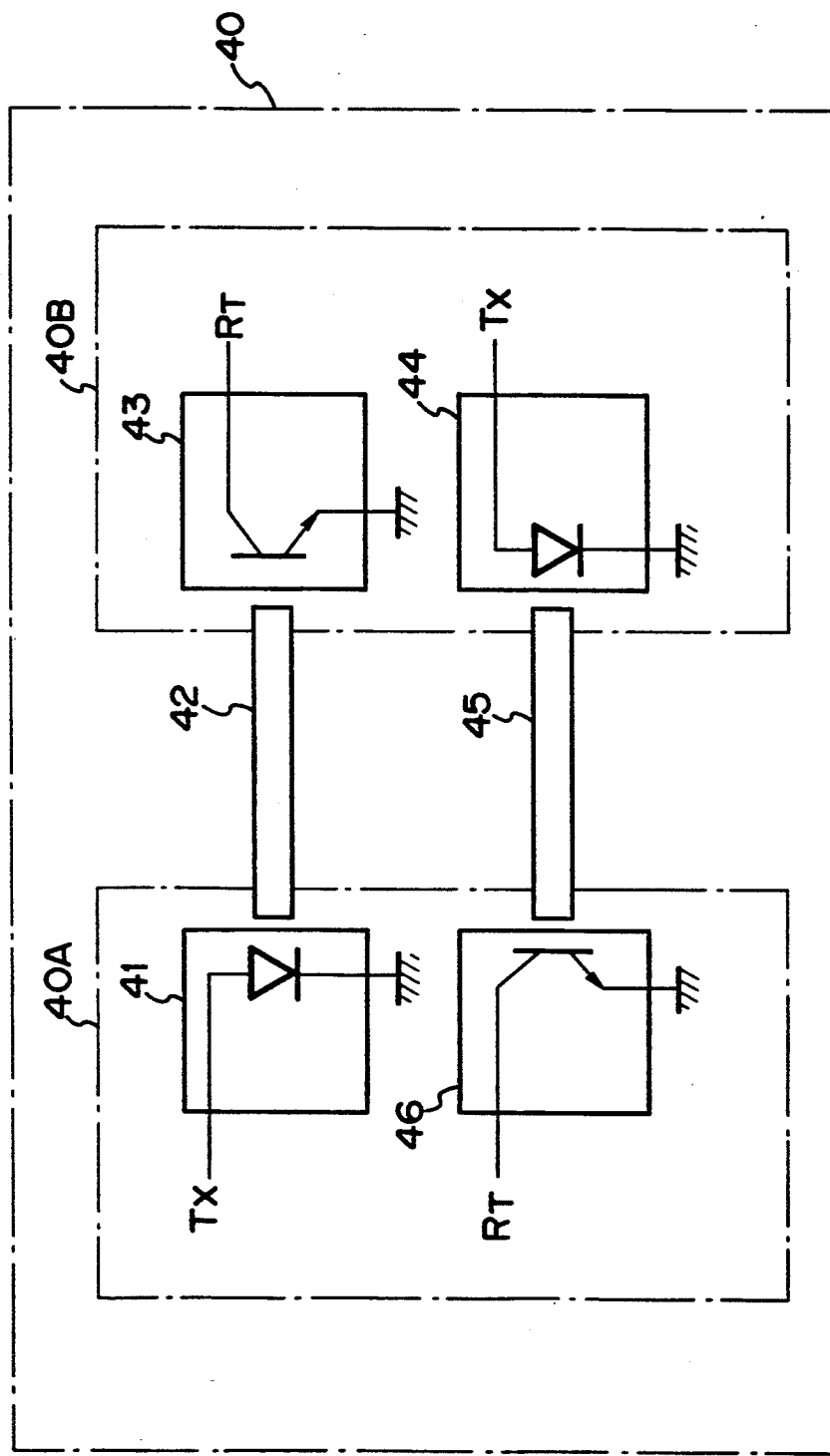
F I G. 4

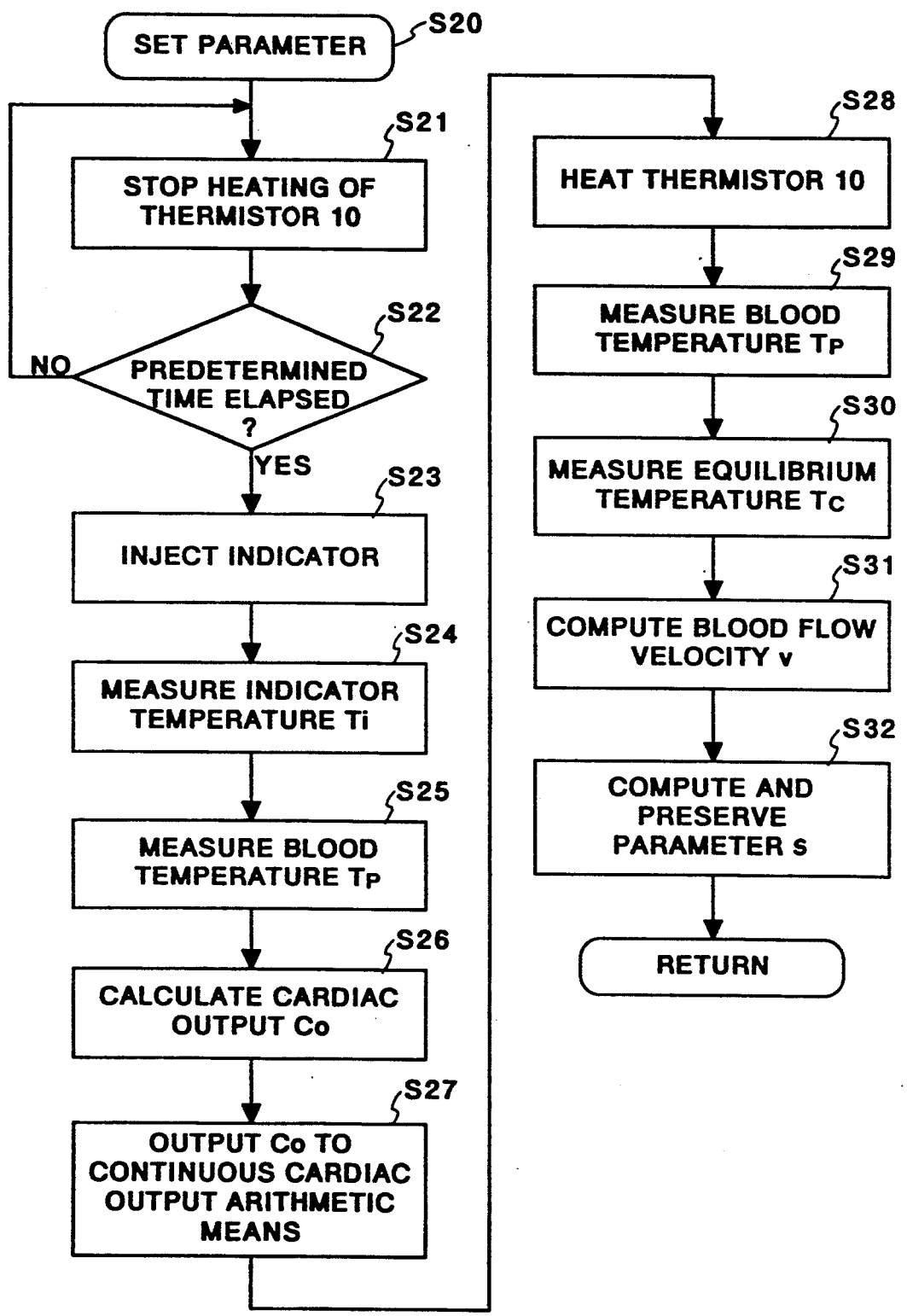
F I G. 7

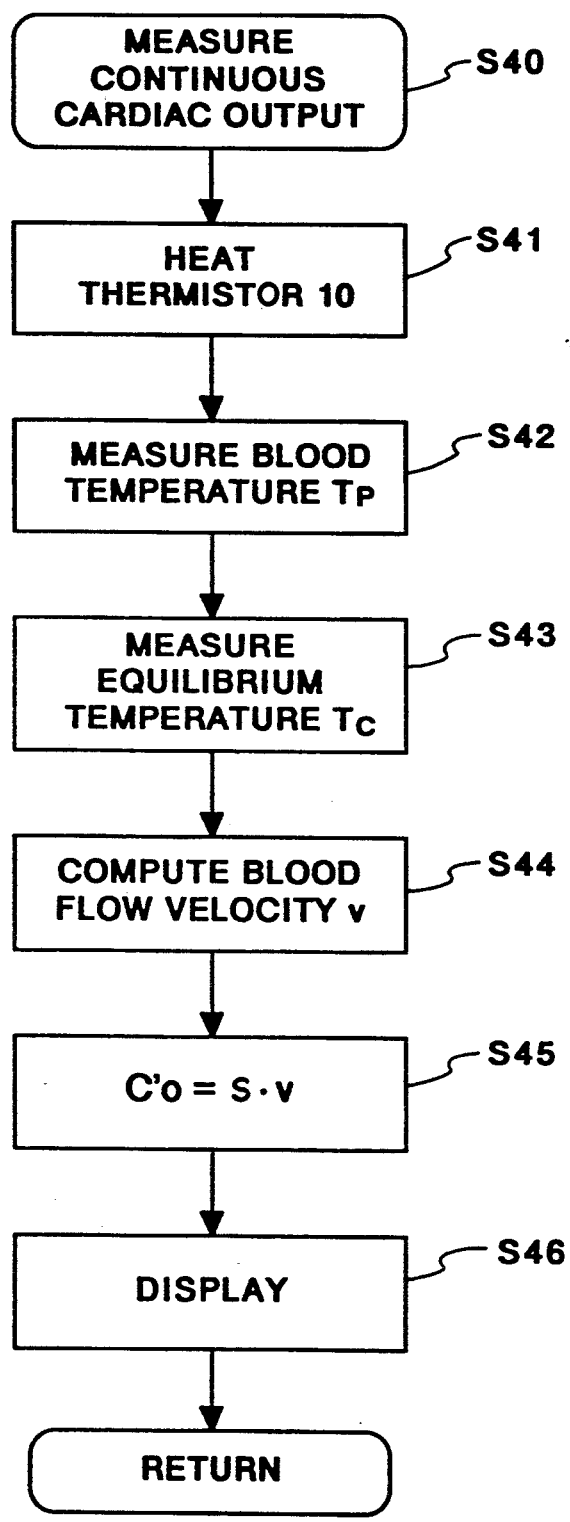
F I G. 8

BIOLOGICAL INFORMATION MEASUREMENT APPARATUS

This application is a continuation of application Ser. No. 07/415,238, filed Sep. 5, 1989, now abandoned.

BACKGROUND OF THE INVENTION

1. Field of the Invention

This invention relates to a biological information measurement apparatus and, more particularly, to a biological information measurement apparatus for measuring biological information safely and easily by contacting a probe with the surface of a living body or inserting the probe directly into the living body.

2. Description of the Related Art

In general, with a biological information measurement apparatus of this kind, particularly a measurement apparatus for medical purposes, safety measures are of paramount importance, in comparison with other types of industrial measurement apparatus. Since a commercial (AC) power supply is used in a biological information measurement apparatus, there is the possibility that a patient or operator will receive an electric shock if electrically connected to the commercial (AC) power supply. The greatest danger involving this electric shock is that of ventricular fibrillation caused by an electric current flowing into the body. Death will result if such ventricular fibrillation is left to continue for two to three minutes. In particular, in measurement of cardiac output of the type in which a catheter is inserted directly into the heart, an accident can cause all of the electric current to flow into the heart through the catheter. For this reason, safety must be given the greatest consideration. In this case, it has been reported that a safe value of current that can flow directly into the heart is on the order of 10 $\mu$A–20 $\mu$A. It has also been reported that the value is less than 500 $\mu$A even between skins having a comparatively high resistance. In this respect, conventional safety measures involve using, say, a power supply transformer provided with double insulation to sufficiently cut off the power supply circuit of the apparatus main body from the commercial (AC) power supply circuit, and grounding the apparatus main body. Conventional safety measures also include grounding one side of a measurement electrode circuit.

However, these one-sided safety measures alone provide no assurance that minute leakage on the order of tens of microamps can be prevented at all times. There is also a type of measurement in which current must be positively passed into a detecting circuit such as a probe. Relying upon a transformer at one location for the purpose of isolation cannot be considered a sufficient safety measure in view of problems involving the layout of the apparatus contacting the power supply section, the aging of the apparatus and the environment in which the apparatus is used. In addition, a living body is not always at ground potential, and there are cases where forcibly placing a living body at ground potential can be more dangerous instead.

In recent years, various types of electronic sensors (temperature sensors, light sensors, pressure sensors and ion sensors, etc.) have been developed, and these sensors are widely applied in the aforementioned biological measurement apparatus, particularly in a variety of electronic measurement apparatus for medical purposes. Most of these sensors utilize a change in the electrical characteristics (quantity of electricity) of a sensor element, but in general it is difficult to make the electrical characteristics perfectly uniform for each and every sensor element. Consequently, the practice in the prior art is to select and use those sensor elements whose electrical characteristics are most uniform. An alternative practice is to correct for variances in electrical characteristics of sensor elements in each and every measurement apparatus by using a corrective characteristic element.

In general, since a probe is easily consumed, it is desired that probes be made readily replaceable. However, when it is attempted to effect a correction for each and every probe in advance, there is a limitation upon this type of correction. Therefore, when a measurement requiring high precision is carried out, conformity between the probe and the main body of the measurement apparatus becomes a major problem.

SUMMARY OF THE INVENTION

The present invention has been devised in order to solve the aforementioned problems of the prior art and its object is to provide a biological information measurement apparatus capable of performing measurement with greater safety under all measurement conditions and in all measurement environments.

Another object of the present invention is to provide a biological information measurement apparatus in which, any leakage current of AC or DC from detecting means is automatically recognized, thereby making it possible to improve the safety of measurement.

Another object of the present invention is to provide a biological information measurement apparatus in which, even if a a probe or catheter is replaced, the electrical characteristics of the detecting element thereof can be readily identified, thereby making it possible to apply a corrective reference table or the like appropriate for the pertinent probe, etc.

In order to attain the foregoing objects, the biological information processing apparatus of the present invention comprises a biological information detecting circuit for electrically detecting biological information and outputting a digital signal indicative of the biological information, a biological information processing circuit for digitally processing the biological information based on the outputted digital signal, and signal transmission means interposed between the biological information detecting circuit and the biological information processing circuit for performing an exchange of signals between these circuits in an electrically isolated state.

In a preferred embodiment, the signal transmission means employs light as a signal transmission medium.

Further, in order to attain the foregoing objects, the biological information processing apparatus of the present invention comprises a biological information detecting circuit for electrically detecting biological information, a first power supply circuit for supplying power solely to the biological information detecting circuit, a second power supply circuit for supplying power to the first power supply circuit, and power transmission means interposed between the first power supply circuit and the second power supply circuit for supplying the power from the second power supply circuit to the first power supply circuit in an electrically isolated state.

In a preferred embodiment, the power transmission means is a transformer in which a primary winding circuit and a secondary winding circuit are electrically isolated from each other.

Further, in order to attain the foregoing objects, the biological information processing apparatus of the present invention comprises a detecting element for electrically detecting biological information and outputting an electric signal indicative of the biological information, a biasing circuit for applying electrical bias to the detecting element, and leakage current detecting means for detecting whether leakage current is present in a living body by detecting and comparing a value corresponding to a current value applied to the detecting element and a value corresponding to a current value fed back to the biasing circuit via the detecting element.

In a preferred embodiment, the leakage current detecting means has a current detecting element in each of a current circuit on a side in which current flows from the biasing circuit into the detecting element and a current circuit on a side in which current is fed back from the detecting element to the biasing circuit.

Further, in order to attain the foregoing objects, the biological information processing apparatus of the present invention comprises a probe having a detecting element for electrically detecting biological information and a corrective element for correcting electrical characteristics of the detecting element, a biasing circuit for applying a predetermined bias solely to the corrective element in the probe, a reading circuit for reading a quantity of electricity of the corrective element corresponding to the applied bias, and recognition means for recognizing the type of probe connected by comparing the read quantity of electricity and a predetermined value.

In a preferred embodiment, the recognition means recognizes the fact that a probe is not connected when the read quantity of electricity exceeds a predetermined range.

BRIEF DESCRIPTION OF THE DRAWINGS

FIG. 4 is a circuit diagram illustrating an opto-isolation transmission circuit of the embodiment;

FIG. 7 is a flowchart illustrating the details of a processing routine for setting a parameter s in the embodiment; and FIG. 8 is a flowchart illustrating the details of a continuous cardiac output measurement routine of the embodiment.

DESCRIPTION OF THE PREFERRED EMBODIMENT

An embodiment of the present invention will now be described in detail with reference to the accompanying drawings.

Figure 1:
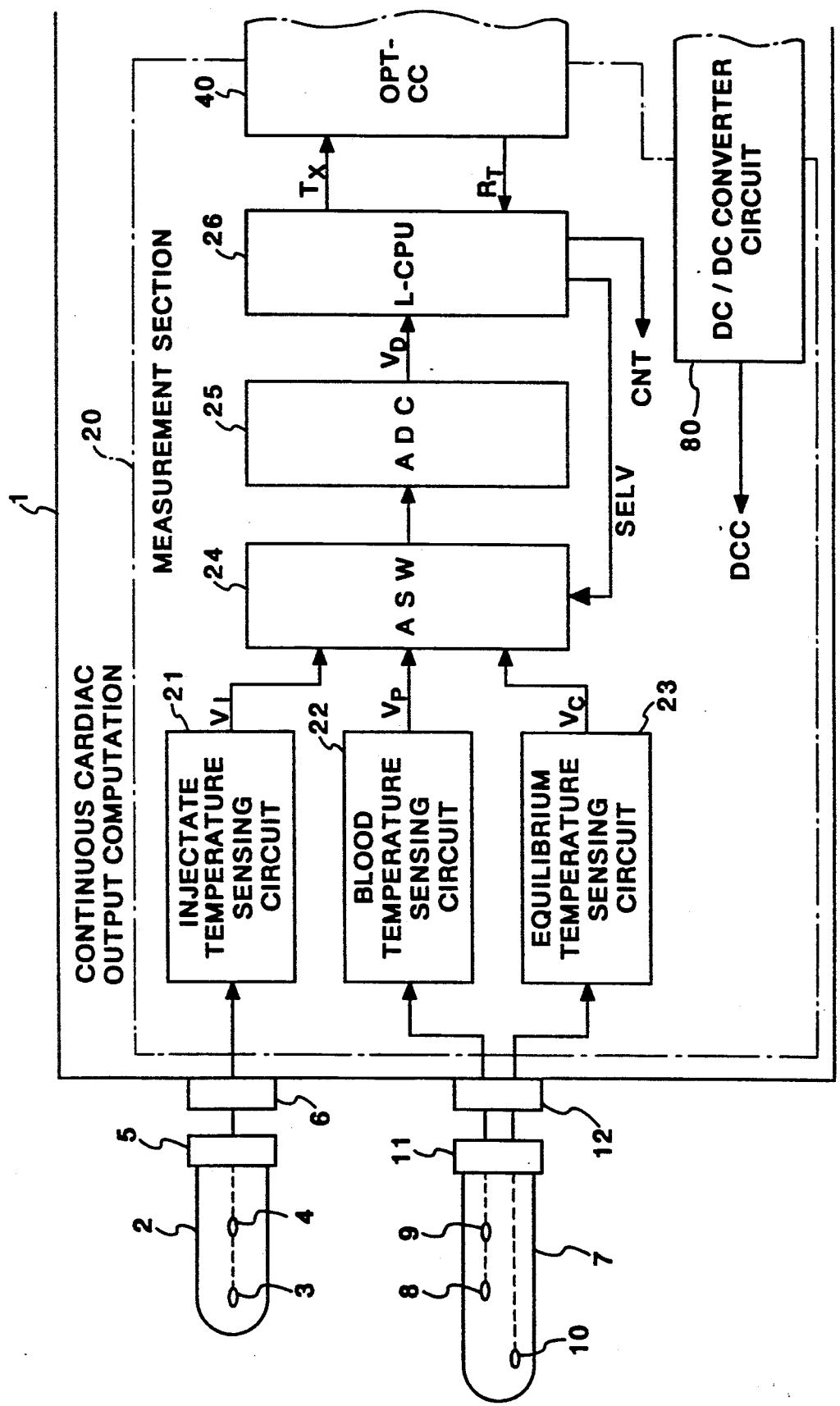
FIGS. 1(A) and 1(B) are block diagrams illustrating a continuous cardiac output measurement apparatus of an embodiment according to the present invention.

FIG. 1 is a block diagram illustrating a continuous cardiac output measurement apparatus of an embodiment according to the present invention. In FIG. 1, numeral 1 denotes the main body of a continuous cardiac output measurement apparatus to which freely replaceable catheters 2, 7 for measuring cardiac output are externally connected. Of the two catheters, the catheter 2 is for injecting an indicator and detecting the temperature of the indicator based on the thermal dilution method. This catheter has an internal probe circuit for sensing the temperature of a medical fluid, the circuit comprising a temperature-sensitive element (a thermistor or the like) for sensing the temperature of the indicator, and a corrective resistor 4 which corrects for a variance in characteristics from one temperature-sensitive element to another. The medical fluid temperature sensing probe circuit is electrically connected to a measurement section 20 of main body 1 via connectors 5 and 6 and is positioned in the right atrium of the heart when cardiac output is measured. The catheter 7 is for sensing blood temperature and blood flow velocity. Provided within the catheter 7 are a blood temperature sensing probe circuit comprising a thermistor 8 for sensing a thermally diluted medical fluid (blood) temperature in the right atrium and right ventricle of the heart and a corrective resistor which corrects for a variance in characteristics from one thermistor to another, and a blood flow velocity sensing probe circuit comprising a thermistor 10 (preferably a self-heating thermistor) positioned 5-20 mm downstream or upstream of the thermistor 8 in terms of blood-flow direction for sensing blood flow velocity by the so-called thermal equilibrium method. The blood temperature sensing probe circuit and blood flow velocity sensing probe circuit are electrically connected to the measurement section 20 via connectors 11 and 12 and are situated in the pulmonary artery when measuring cardiac output.

The catheters 2 and 7 are manufactured as a unitary body in terms of outward appearance. Alternatively, it can be arranged so that only the indicator injecting mechanism portion of the catheter 2 is provided unitarily with the catheter 7, with the remaining medical fluid temperature sensing probe circuit (catheter 2) being constructed as a separate, independent unit. This remaining circuit is inserted into an injectate tank. Reference can be had to Japanese Patent Application No. 61-48681 with regard to the construction of part of such a catheter and the usage thereof.

The main body 1 is largely broken down into a number of units. Specifically, these are the measurement section 20 for executing various temperature measurements via the catheters 2 and 7, an opto-isolation communication circuit (OPT-CC) 40 for transmitting measurement data, obtained by the measurement section 20, by optical means, a main CPU 30 for computing values of cardiac output intermittently by the thermal dilution method or continuously by blood flow velocity measurement based on the measurement data inputted via the opto-isolation communication circuit 40, and for outputting the results of these computations, a display unit 50 for displaying the value of cardiac output determined by the computations in the main CPU 30, and a power source unit 70 for supplying DC power to each of the aforementioned units of the main body 1.

In the measurement section 20, numeral 21 denotes a circuit for sensing the temperature of an injected fluid. This circuit detects a temperature $T_I$ of an indicator discharged into the right atrium from an aperture (not shown) in the catheter 2, and outputs a corresponding voltage signal $V_I$. Alternatively, the circuit 21 is inserted into an injectate tank to detect the indicator temperature $T_I$ and output the corresponding voltage signal $V_I$. Numeral 22 denotes a circuit for sensing blood temperature. This circuit detects a temperature $T_P$ of a medical fluid (blood) that is thermally diluted by the time the indicator, which is discharged into the right atrium, reaches the pulmonary artery, and outputs a corresponding voltage signal $V_P$. Numeral 23 denotes a circuit for sensing equilibrium temperature. This circuit sensing thermal equilibrium between an amount of heat applied by, e.g., the self-heating thermistor 10, and an amount of heat taken away by the peripheral blood, and outputs a corresponding voltage signal $V_C$ ($V_{CL}$, $V_{CM}$, $V_{CH}$). Numeral 26 denotes a local CPU (L-CPU) which, in accordance with instructions from the main CPU 30, outputs various control signals CNT, which are for executing the instructions, to the sensing circuits for controlling the above-described measurement operations of the injected fluid temperature sensing circuit 21, the blood temperature-sensing circuit 22 and the equilibrium blood temperature sensing circuit 23. The output signals of an analog switch (ASW) 24 are selected by a selection signal SELV from the local CPU 26, the selected signals are converted into digital data VD by an A/D converter (ADC) 25, and these data are accepted into the local CPU 26. Further, the local CPU 26 Co internally equipped with a serial communication function via which various command signals $R_T$ from the main CPU 30 are accepted and the digital data VD received from the sensing circuits are converted into serial transmission data $T_x$ and sent to the main CPU 30.

The purpose of the opto-isolation communication circuit 40 is to implement an exchange of signals between the measurement section 20 and the main CPU 30 in a completely isolated state electrically speaking. For example, as shown in FIG. 4, the opto-isolation communication circuit 40 is equipped, in a mutually electrically isolated state, with a light sending/receiving circuit 40A comprising a photodiode circuit 41 and a phototransistor circuit 46 provided on the side of the measurement section, and a light sending/receiving circuit 40B comprising a photodiode circuit 44 and a phototransistor circuit 43 provided on the side of the main CPU 30. Optical fiberglass 42, 45 is interposed between these two circuits as a medium for transmitting the signals between them. Accordingly, the electrical connection between the electric signals of the measurement section 20 and the electric signals of the CPU 30 is completely cut off. As a result, measurement can be performed safely because there is no danger of any closed loop being formed between a living body and the apparatus on the side of the main CPU 30.

In the main CPU 30, blocks, which are described below, indicate various functional blocks implemented by execution of the programs of FIGS. 6 through 8 by the main CPU 30. Here numeral 31 denotes arithmetic means for computing cardiac output by thermal dilution. The arithmetic means 31 receives as inputs the injectate temperature $T_I$ of the indicator and the thermally diluted blood temperature $T_P$, computes a thermal dilution cardiac output $C_o$ and outputs the result. Numeral 32 denotes arithmetic means for computing blood flow velocity. The arithmetic means 32 continuously receives as inputs the thermal equilibrium temperature $T_C$ of the heating thermistor 10 and the blood temperature $T_P$, computes blood flow velocity v and outputs the result. Numeral 33 denotes arithmetic means for continuously computing cardiac output. Based on the thermal dilution cardiac output $C_o$, obtained by the cardiac output arithmetic means 31 on the basis of the thermal dilution method, and the blood flow velocity v obtained by the blood flow velocity arithmetic means 32, the continuous cardiac output arithmetic means 33 computes a blood vessel cross-section area parameter s indicative of the pulmonary artery, saves this parameter in a register S-REG, then computes a continuous cardiac output $C_o'$ based on the blood velocity v, which is obtained by the blood flow velocity arithmetic means 32, and the blood vessel cross-sectional area parameter s preserved in the register S, and then outputs the result.

Figure 5:
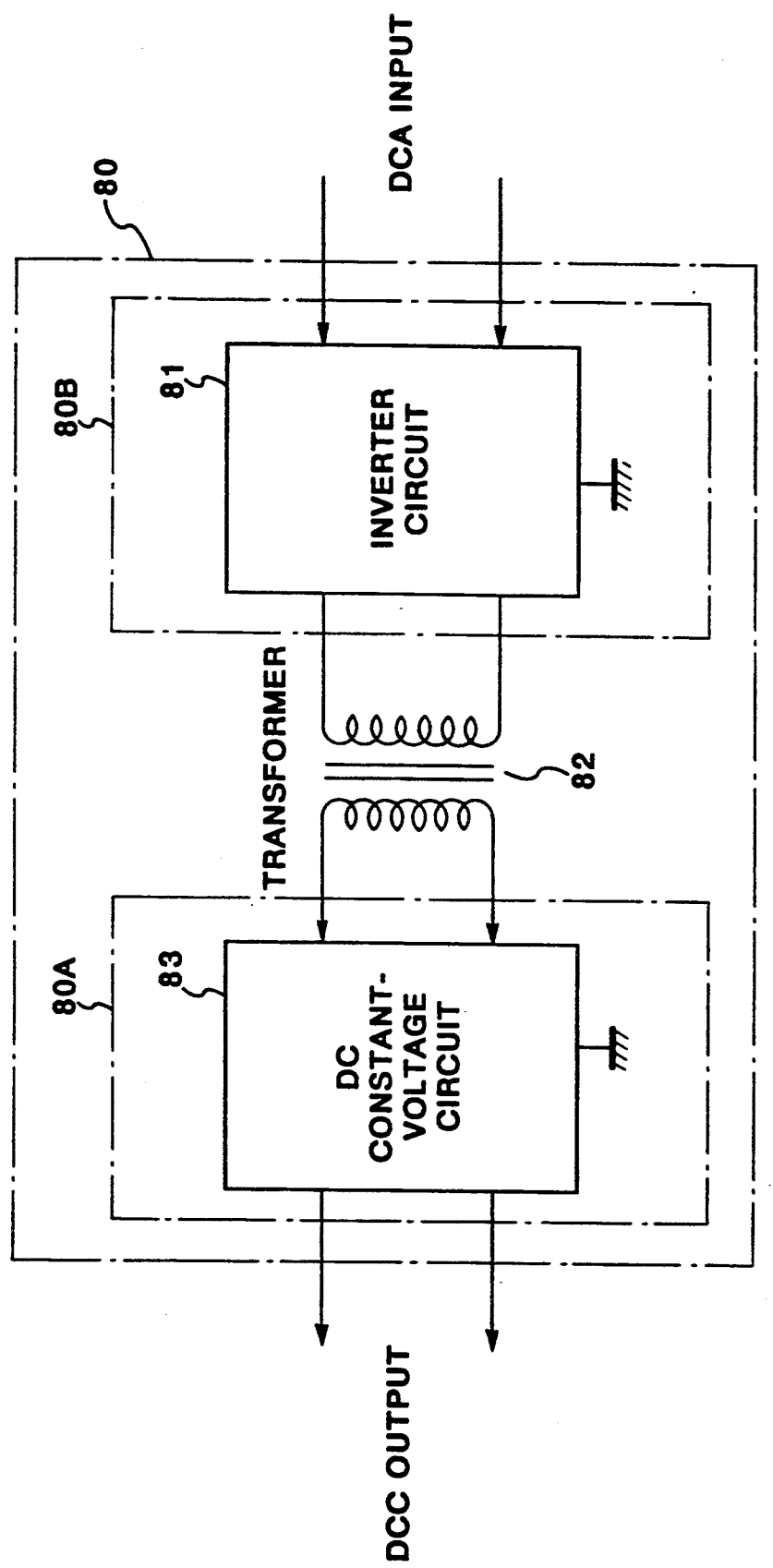
FIG. 5 is a circuit diagram illustrating a DC/DC converter circuit of the embodiment.

In the power supply section 70, numeral 71 denotes an alternating current (AC) power supply transformer which steps down an externally applied AC input voltage (100 V, 50/60 Hz, etc.) to convert the same to a predetermined AC output voltage. The primary winding and secondary winding of the power supply transformer 71 are coupled magnetically only, so that an electrical connection between the main body 1 and the external AC input circuitry is cut. Numeral 72 denotes a DC power supply circuit for smoothing the predetermined AC output voltage of the power supply transformer 71, stabilizing the same, converting it into a DC voltage and then supplying a DC voltage DCA to a DC/DC converter circuit 80 and a DC voltage DCB to the main CPU 30. The purpose of the DC/DC converter circuit 80 is to see to it that the supply of power from the power supply section 70 to the measurement section 20 is performed in a perfectly isolated state electrically speaking. For example, as shown in FIG. 5, the DC/DC converter circuit 80 is equipped, in a mutually electrically isolated state, with an inverter circuit 81 for temporarily converting the DCA input supplied by the side of the power supply 70 (80B) into AC power and then outputting the same, and a DC constant-voltage circuit 83 for supplying a direct-current DCC output stabilized on the side of the measurement section 20 (80A). Interposed between the circuits 80A, 80B is a transformer 82, whose primary and secondary windings are coupled magnetically only, as means for transmitting power from the inverter circuit 81 to the DC constant-voltage circuit 83. Accordingly, an electrical connection between the DC power supply circuitry of the measurement section 20 and the power supply circuitry of the power supply section 70 is completely cut. As a result, measurement can be performed safely because there is no danger of any closed loop being formed between a living body and the main body 1 or the external AC power input circuitry.

Figure 2:
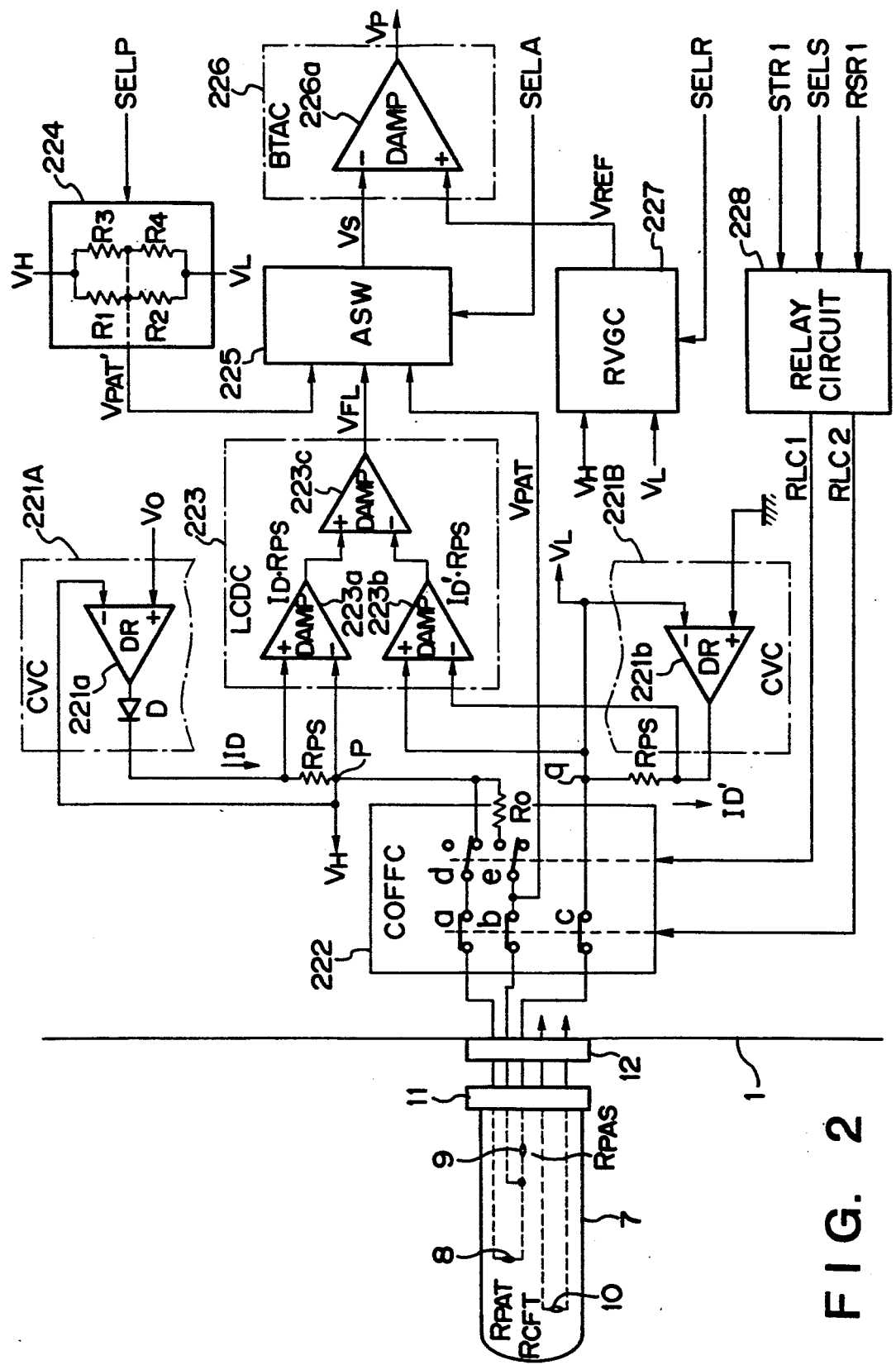
FIG. 2 is a circuit diagram illustrating the details of a blood temperature sensing circuit 22 of the embodiment.

FIG. 2 is a circuit diagram illustrating the details of the blood temperature sensing circuit 22 of the embodiment. It should be noted that the injectate temperature sensing circuit 21 is approximately the same as the blood temperature sensing circuit 22 and therefore need not be described.

In FIG. 2, the local CPU 26 turns on a relay circuit 228 in advance by means of a control signal STR1. In response, the relay circuit 228 outputs a control signal RLC2 and places contacts a, b and c of a current cut-off circuit (COFFC) 222 in the closed state. Further, the local CPU 26 applies a selection signal to the relay circuit 228 in advance by a control signal SELS. In response, the relay circuit 228 outputs a selection signal RLC1 to connect contacts d and e of the current cut-off circuit 222 to the lower side, as illustrated.

In this state, a constant-voltage circuit (CVC) 221A applies a constant potential $V_H$ to the thermistor 8.

More specifically, by referring to an input reference voltage $V_O$, a driver (DR) 221a of the constant-voltage circuit 221A performs a driving operation in such a manner that the potential at a point p will become approximately $V_O$. Accordingly, the potential at the point p is held at the contant potential $V_H$ (approximately $V_O$) at all times. A constant-voltage circuit (CVC) 221B applies a potential $V_L$ to the corrective resistor 9. That is, by referring to an input reference voltage GND, a driver (DR) 221b of the constant-voltage circuit 221B performs a driving operation in such a manner that the potential at a point q will become approximately GND. Accordingly, the potential at the point q is held at the contant potential $V_L$ (approximately GND) at all times. Thus, a constant voltage ($V_H$-$V_L$) is applied at all times to the series circuit composed of the thermistor 8 and corrective resistor 9 of the catheter 7.

When cardiac output is measured, the thermistor 8 experiences a change in its resistance value $R_{PAT}$ in accordance with thermally diluted blood temperature, and the aforementioned constant voltage ($V_H$-$V_L$) is divided by the corrective resistance value $R_{PAS}$, whereby the resulting voltage (blood-temperature signal) $V_{PAT}$ is outputted to an analog switch (ASW) 225. The blood-temperature signal $V_{PAT}$ is selected by a control signal SELA from the local CPU 26 and is passed through the analog switch 225 to enter a ($-$) terminal of a differential amplifier 226a of a blood temperature amplifier circuit (BTAC) 226. Meanwhile, a reference voltage generator circuit (RVGC) 227 selects the constant potential $V_H$ in accordance with a control signal SELR from the local CPU 26, and this potential is applied as a reference voltage $V_{REF}$ to a ($+$) terminal of the differential amplifier 226a. As a consequence, the value of the divided voltage $V_{PAT}$ applied across the ($+$) and ($-$) terminals of the differential amplifier 226a is decided by the following equation:

$$V_{PAT} = \frac{(V_H - V_L) \cdot R_{PAT}}{R_{PAT} + R_{PAS}} \quad (1)$$

Eq. (1) clearly shows that when this divided voltage $V_{PAT}$ is employed, the non-linear resistance value $R_{PAT}$ of the thermistor 8 appears in both the numerator and denominator, and the corrective resistance value $R_{PAS}$ conforming to inherent resistance value $R_{PAT}$ of the thermistor 8 appears in the denominator. Therefore, the linearity of the probe circuit and the resistance value with respect to a predetermined temperature are corrected. The differential amplifier 226a amplifies the divided voltage $V_{PAT}$ and outputs a blood temperature signal $V_P$.

When the probe circuit is driven at a constant current $I_C$, it will suffice to effect a correction upon connecting the thermistor 8 and corrective resistor 9 in parallel. As a result, a back emf $V_{PAT}'$ impressed across the ($+$) terminal and ($-$) terminal of the differential amplifier 226a is decided by the following equation:

$$V_{PAT}' = \frac{I_C \cdot R_{PAS} \cdot R_{PAT}}{R_{PAT} + R_{PAS}} \quad (1')$$

Eq. (1') clearly shows that the non-linear resistance value $R_{PAT}$ of the thermistor 8 appears in both the numerator and denominator, and the corrective resistance $R_{PAS}$ conforming to inherent resistance value $R_{PAT}$ of the thermister 8 appears in both the numerator and denominator. Therefore, the linearity of the probe circuit and the resistance value with respect to a predetermined temperature are corrected.

By way of example, the characteristics of the thermistors 3 and 8 of the embodiment are $B_{25-45} = 3970$ K, $R(37) = 40$ KΩ, and the size thereof is $0.50^1 \times 0.16^w \times 0.15^t$ (millimeter units). Also, $B_{25-50} = 3500$ K, $R(37) = 40$ KΩ, and the size thereof is $0.75^1 \times 0.16^w \times 0.15^t$. Further, the characteristics of the thermistor 10 are $B_{25-45} = 3500$ K, $R(37) = 1000$ Ω, and the size thereof is $1.18^1 \times 0.4^w \times 0.15^t$.

However, these thermistor characteristics do not pose a restriction on the invention, and it is possible to use catheters of different types. In particular, even if there is a variance in the non-linear characteristics and resistance values with respect to a predetermined temperature in the thermistors 3 and 8, or even if the ratings of the thermistors themselves differ, the resistor temperature characteristics are corrected in advance by the corrective resistors 4, 9 provided in the catheters 2, 7. Therefore, the temperature - resistance characteristics as seen from the side of the main body 1 are handled identically.

It is desired that the amount of heat produced by the thermistor 10 in a case where this thermistor is of the self-heating type range from 0.01 to 50 joules. With a large amount of generated heat, there is the possibility that the blood temperature will rise or that damage will be caused to the walls of the blood vessels. With a small amount of generated heat, there will be too little detection sensitivity. Neither of these alternatives is desirable.

A leakage current detecting circuit (LCDC) 223 detects whether leakage has occurred in a current $I_D$ flowing through a constant-voltage loop. The constant-current loop includes two current detecting resistors $R_{PS}$ of identical value inserted serially in the loop. Differential amplifiers (DAMP) 223a, 223b of the leakage current detecting circuit 223 are for differentially amplifying back emf's ($I_D \cdot R_{PS}$) and ($I_D' \cdot R_{PS}$) which appear across each of the resistors $R_{PS}$. In this case, current $I_D$ on the source side and current $I_D'$ on the sink side will be equal if there is no leakage of current in the constant-voltage loop. Accordingly, the output voltages of the differential amplifiers 223a, 223b also become equal, and the output signal $V_{FL}$ of a differential amplifier 233c is 0 V. On the other hand, if leakage develops in the constant-voltage loop via the catheter 7, the prevailing state becomes $I_D > I_D'$ (outflow) or $I_D < I_D'$ (inflow) and the outputs of the differential amplifiers 223a, 223b become related as follows: ($I_D \cdot R_{PS}$) > ($I_D' \cdot R_{PS}$) or ($I_D \cdot R_{PS}$) < ($I_D' \cdot R_{PS}$). As a result, the output signal of the differential amplifier 233c fluctuates by $\pm V_{FL}$. Accordingly, the local CPU 26 makes the reference voltage generating circuit 227 to generate a suitable reference voltage $V_{FRE}$, whereby it is possible to periodically investigate the extent and state of the leakage current. When the local CPU 26 determines that a leakage current exists, it sends a control signal RSR1 to the relay circuit 228. In response, the relay circuit 228 outputs the control signal RLC2 to immediately open the contacts a~c of the current cut-off circuit 222. Accordingly, supply of current to the probe circuit is immediately interrupted. This eliminates any adverse effect upon a living body.

It is also possible to sense current as by a Hall device. In addition, if the probe circuit is biased by alternating current, current can be detected by a coil wound on the current loop.

A reference resistor circuit 224 outputs the reference temperature signal $V_{PAT}'$ for calibrating the blood temperature sensing circuit 22. By transmitting a control signal SELP, the local CPU 26 makes the reference resistor circuit 224 to output the reference temperature signal $V_{PAT}'$ corresponding to the predetermined temperature $T_1$ or $T_2$. Dividing resistors $R_1 \sim R_4$ in the reference circuit 224 have predetermined resistance values, and these resistance values hardly vary with temperature. Constant potentials $V_H$ and $V_L$ are applied to respective ones of the serial resistance networks ($R_1$ and $R_2$, $R_3$ and $R_4$, etc.). For this reason, temperature drift of the analog circuit network (analog switch 225, blood temperature sensing circuit 226, etc.) is detected under conditions the same as those of the probe circuit of catheter 7. This makes it possible to correct actually detected temperature. More specifically, when a temperature $T_1'$ is sensed when the reference resistor circuit 224 is made to generate a value corresponding to the predetermined temperature $T_1$, information relating to an error $\Delta T = (T_1' - T_1)$ is obtained by the main CPU 30, whereby a temperature reference table or the like is used upon being shifted or corrected.

Before measurement starts, the local CPU 26 transmits the control signal SELS to the relay circuit 228 to connect the contacts d and e of the current cut-off circuit 222 to the upper side in FIG. 2. As a result, the circuit for feeding current to the thermistor 8 is opened and the constant voltage $(V_H - V_L)$ is applied to the corrective resistor 9 via a reference resistor $R_O$ instead. In this case, the value of the reference resistor $R_O$ is already known within the main CPU 30 and is constant. The value of the corrective resistor $R_{PAS}$, however, differs depending upon the correction applied to the thermistor 8. Accordingly, the local CPU 26 (main CPU 30) accepts the divided voltage $V_{PAT}$ prevailing at this time, whereby the characteristics of the thermistor 8 can be investigated. For example, when the divided voltage $V_{PAT}$ exhibits variance within a prescribed range, it can be judged that the type of thermistor 8 (the type of catheter 7) is identical. However, when the divided voltage $V_{PAT}$ exhibits an extreme difference, it can be judged that the thermistor 8 belongs to a different category. If it has been decided that such a catheter of different type will be used with the main body 1 of the apparatus, the main CPU 30 will use a temperature reference table shifted or selected in accordance with the results of judgment.

When the divided voltage $V_{PAT}$ is equal to the reference voltage $V_{REF}(=V_H)$, it can be judged that a wire has broken in the probe circuit within the catheter 7 or that the catheter itself has not been connected. Thus, the local CPU 26 (main CPU 30) sequentially investigates the states of the various sensing circuits before, during and after measurement and automatically deals with the states detected.

Figure 3:
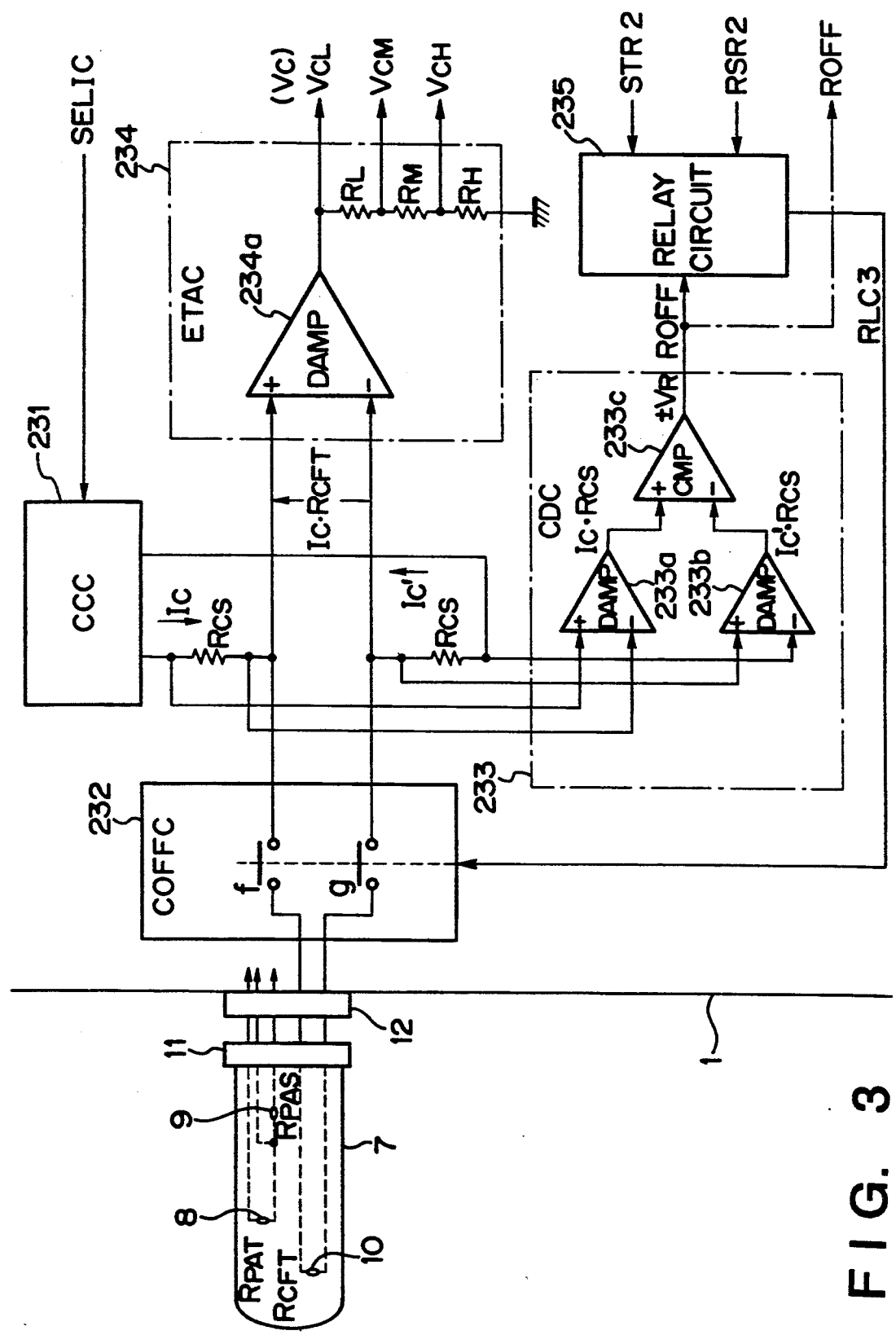
FIG. 3 is a circuit diagram illustrating the details of an equilibrium temperature sensing circuit 23 of the embodiment.

FIG. 3 is a circuit diagram illustrating the details of the equilibrium temperature sensing circuit 23 of the embodiment.

The local CPU 26 turns on a relay circuit 235 in advance by a control signal STR. In response, the relay circuit 235 outputs a control signal RLC3 to place contacts f and g of a current cut-off circuit (COFFC) 232 in the closed state. Further, the local CPU 26 sets the magnitude of a contant current $I_C$ of a constant-current circuit (CCC) 231 by a control signal SELIC. In response, the constant current circuit 231 supplies the set constant current $I_C$ to the constant-current loop containing the thermistor 10. As a result, the thermistor 10 is heated up by the constant current $I_C$ and its resistance value $R_{CFT}$ varies in accordance with equilibrium temperature between the amount of heat applied to the surrounding blood and the amount of heat absorbed by the surrounding blood. A detection voltage $(I_C R_{CFT})$ indicative of this equilibrium temperature is applied to the input of a differential amplifier (DAMP) 234a of an equilibrium temperature amplifier circuit (ETAC) 234. The differential amplifier 234a differentially amplifies the detection voltage $(I_C R_{CFT})$ and forms an output voltage $V_{CL}$ indicative of the thermal equilibrium temperature. The output circuit of the differential amplifier 234a provided with resistors $R_L$, $R_M$, $R_H$ are dividing resistors for dividing the output voltage $V_{CL}$. These change the measurement range to a medium range $V_{CM}$ or high range $V_{CH}$ depending upon the magnitude of the thermal equilibrium temperature, so that the maximum resolution of the A/D converter 25 is made to correspond to the particular measurement range.

Since the magnitude of the set constant current $I_C$ is already known within the main CPU 30, the latter obtains the thermal equilibrium resistance value $R_{CFT}$ of thermistor 10 in accordance with the equation $R_{CFT} = V_C/I_C$.

A leakage current detecting circuit (LCDC) 233 detects whether leakage has occurred in the constant current $I_C$ flowing through the constant-current loop. The constant-current loop includes two current detecting resistors $R_{CS}$ of identical value inserted serially in the loop. Differential amplifiers 233a, 233b of the leakage current detecting circuit 233 are for differentially amplifying back emf's $(I_C \cdot r_{CS})$ and $(I_C' \cdot R_{CS})$ which appear across each of the resistors $R_{CS}$. In this case, current $I_C$ on the source side and current $I_C'$ on the sink side will be equal if there is no leakage of current in the constant-current loop. Accordingly, the output voltages of the differential amplifiers 233a, 233b also become equal. As a result, the inputs to a comparator (CMP) 233c become equal, so that the output signal ROFF thereof becomes approximately 0 V. Hence, the relay circuit 235 remains on. On the other hand, if leakage develops in the constant-current loop via the catheter 7, the prevailing state becomes $I_C > I_C'$ (outflow) or $I_C < I_C'$ (inflow) and the outputs of the differential amplifiers 233a, 233b become related as follows: $(I_C \cdot R_{CS}) > (I_C' \cdot R_{CS})$ or $(E_C \cdot R_{CS}) < (I_C' \cdot R_{CS})$. As a result, the output signal ROFF of the comparator 233c fluctuates by $\pm V_R$. In either case, when the predetermined range is exceeded, the relay circuit 235 is turned off immediately. In response, the relay circuit 235 outputs a control signal RLC3 to immediately open the contacts f, g of the current cut-off circuit 232, and supply of current to the catheter 7 is immediately interrupted. This eliminates any adverse effect upon a living body.

It should be noted that an arrangement can be adopted in which the output signal ROFF of the leakage current detecting circuit 233 is fed into the analog switch 24 of FIG. 1 so that this can be remotely monitored by the local CPU (main CPU 30).

The thermistor 10 is not limited to a self-heating thermistor of the kind described above. An arrangement can be adopted in which an ordinary thermistor is provided near a separate heater to be heated up thereby at the constant current $I_C$. However, the self-heating thermistor is more advantageous in that it is easily incorporated in terms of structure and is capable of stable heat generation and detection because of its structure.

With reference again to FIG. 1, the thermal dilution-type cardiac output arithmetic means 31 is provided with inputs of the injectate temperature $T_I$ from the injectate temperature sensing circuit 21 and the blood temperature $T_P$ of the blood temperature sensing circuit 22, uses the well-known Stewart Hamilton Method to compute the cardiac output $C_o$, according to the thermal dilution method, based on the following Eq. (2), and outputs the computed results to the continuous cardiac output computing means 33:

$$C_o = \frac{S_i \cdot C_i \cdot (T_P - T_I) \cdot V_i}{S_P \cdot C_P \cdot \int_0^\infty T_P dt} \quad (2)$$

where
$C_o$: cardiac output
$S_i$: specific gravity of injectate
$C_i$: specific heat of injectate
$V_i$: amount of injectate
$T_I$: injectate temperature
$T_P$: blood temperature
$S_P$: specific gravity of blood
$C_P$: specific heat of blood $\int_0^\infty \Delta T_P dt$: area of thermal dilution curve The blood flow velocity arithmetic means 32 is provided with inputs of blood temperature $T_P$ from the blood temperature sensing circuit 22 and equilibrium temperature $T_C$ from the equilibrium temperature sensing circuit 23, computes the blood flow velocity v based on the following Eq. (3) and outputs the computed results to the continuous cardiac output arithmetic means 33:

$$v = \frac{I_C \cdot V_C}{K \cdot (T_C - T_P)} \quad (3)$$

where K is a proportional constant.

Based on the following Eq. (4), the continuous cardiac output arithmetic means 33 computes the cross-sectional area s of the pulmonary artery blood vessel from cardiac output $C_o$, obtained by the thermal dilution method, and blood flow velocity v, and preserves the computed value in the parameter register S:

$$s = C_o/v \quad (4)$$

The blood vessel sectional area s of the pulmonary artery is considered to be substantially constant over a logical period of time. Therefore, once the parameter s has been found, the continuous cardiac output $C_o'$ then can be measured.

Now, based on the following Eq. (5), the continuous cardiac output arithmetic means 33 computes the continuous cardiac output $C_o'$ from the parameter s and the then measured blood flow velocity v, and outputs the computed results to the display unit 50:

$$C_o' = s \cdot v \quad (5)$$

Figure 6:
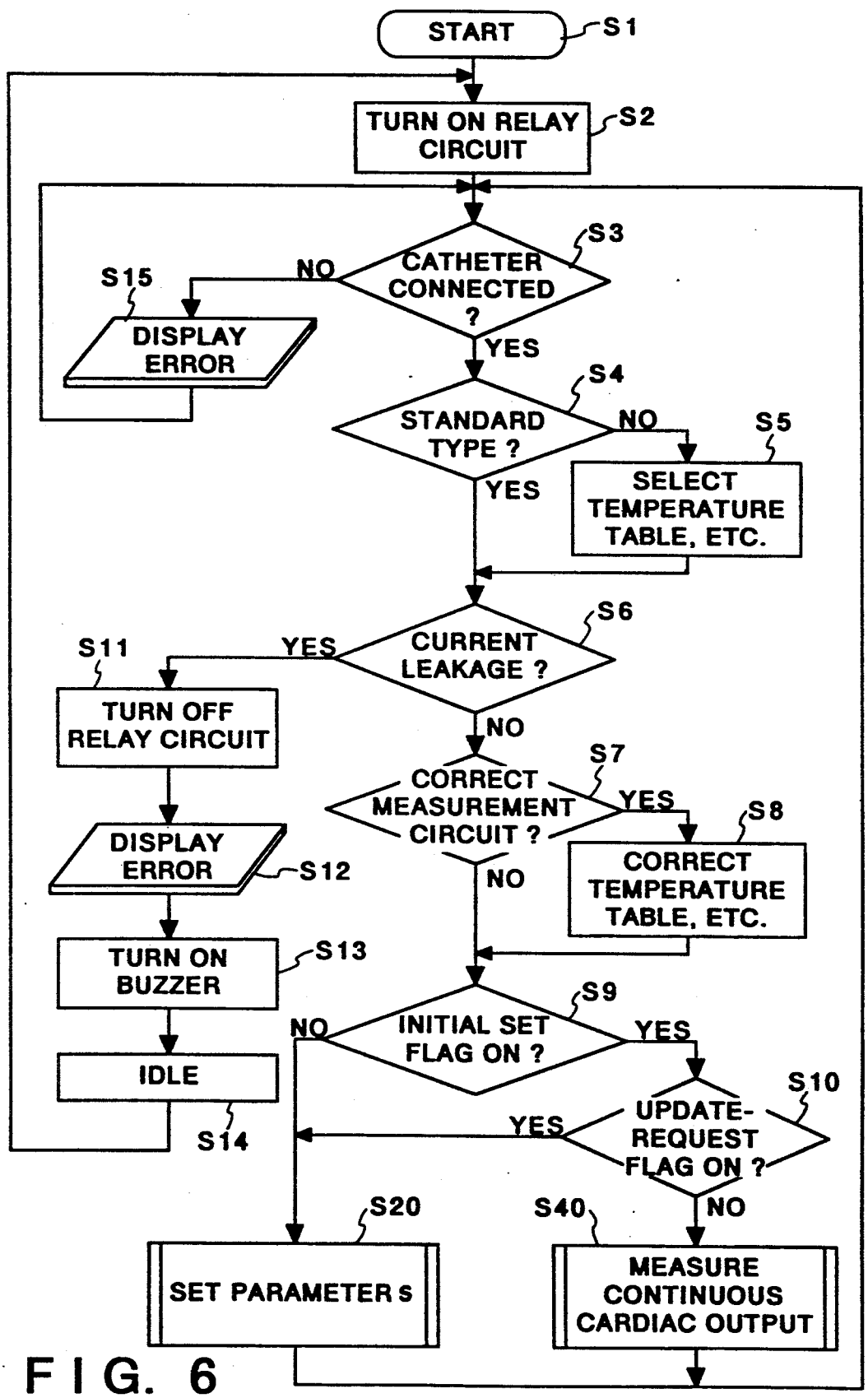
FIG. 6 is a flowchart of a main routine illustrating a cardiac output measurement procedure of the embodiment.

FIG. 6 is a flowchart of a main routine illustrating the continuous cardiac output measurement routine of the embodiment. It should be noted that the processing described hereinbelow is executed with the cooperation of the local CPU 26 based on commands from the main CPU 30.

By introducing power to the apparatus or pressing a measurement start button, the program enters step S1. The relay circuit of each sensing circuit is turned on at step S2. It is investigated at step S3 whether the catheter has been connected by connecting the probe circuit of the catheter to the side of the reference resistor. If the catheter has not been connected, the program proceeds to step S15, an error to this effect is displayed and the program returns to step S3 to see whether the catheter has been connected. If the determination at step S3 is that the catheter has been connected, then it is determined, based on the abovementioned reference resistor, whether the catheter is of the standard type. If it is not of the standard type, the program proceeds to step S5 to select the corresponding temperature table or the like.

When the catheter is of the standard type, the program proceeds to step S6 to investigate whether there is leakage of current in the probe circuit. When it is determined that there is leakage current, the program proceeds to step S11, the relay circuit is turned OFF, an error display to this effect is presented at step S12 and, at step S13, a buzzer 60 is sounded to caution the user. An idle routine is then executed at step S14, abnormalities are eliminated and the system waits until the measurement start button is pressed again. When it is judged that there is no leakage current, the program proceeds to step S7 and it is determined whether it is necessary to correct a measured value using a temperature standard voltage of the measurement circuit.

If a correction is required, the program proceeds to step S8 to correct the temperature table or the like. If a correction is not required, the program proceeds to step S9 to determine whether an initial setting flag of the parameter s is ON or not.

If the flag is not ON, this means that the cardiac output of the patient is starting to be measured or that power has been introduced to the apparatus. The program then proceeds to step S20 where a setting routine for the parameter s is executed. The parameter setting routine involves measuring and computing the cardiac output $C_o$ based on the thermal dilution method, then detecting the blood flow velocity v, computing the parameter s and preserving the result in the parameter register S. Further, the initial value setting flag is turned ON and the program returns to step S3. When the program thus returns to step S9, this time the initial setting flag will have been set the program proceeds to step S10. Step S10 is for determining the necessity of updating the preserved parameter s. This is done by investigating an update-request flag (not shown). For example, setting of the update-request flag may be performed as follows: A timer (not shown) in the main CPU 30 is set in advance to a period of time within which it will become necessary to update the parameter s for reasons of clinical medicine. When this period of time elapses, the update-request flag is set by a timer-interrupt routine or the like. If the update-request flag has been set, the program proceeds to step S20, where a parameter setting routine (in this case, an updating routine) is executed. When the parameter s is thus updated, the aforementioned update-request flag is reset, and the timer is restarted, within this setting routine. If the answer at step S10 is NO, then the parameter s will be effective and reliable. Hence, the program proceeds to step S40 to execute the routine for continuous cardiac output measurement.

FIG. 7 is a flowchart illustrating the details of a processing routine for setting the parameter s in accordance with the embodiment. Heating of the thermistor 10 is halted at step S21. This step has meaning when it is necessary to update the parameter s in the course of continuously measuring cardiac output. Next, at step S22, the thermistor is allowed to cool sufficiently and elapse of a prescribed period of time, namely until there is no longer any influence upon the thermistor 8, is awaited. When the prescribed time period elapses and there is no longer any influence of heating, the program proceeds to step S23, at which a fixed amount of indicator is introduced from the discharge port of the catheter 2. The injectate temperature $T_I$ is measured at step S24. Step S25 calls for measurement of blood temperature $T_P$ thermally diluted by the time the pulmonary artery is reached. At step S26, the cardiac output $C_o$ is computed by the thermal dilution-type cardiac output arithmetic means 31 in accordance with Eq. (2), and the calculated cardiac output $C_o$ is outputted to the continuous cardiac output arithmetic means 33 at step S27. Though not shown, the continuous cardiac output arithmetic means 33 displays the cardiac output value $C_o$ if necessary. Thus is measured the cardiac output $C_o$ based on the thermal dilution method, this being the initial cardiac output or that for updating the parameter s.

Next, at step S28, the thermistor 10 is heated at the constant current $I_C$, and the blood temperature $T_P$ prior to heating is measured at step S29. The equilibrium temperature $T_C$ of the thermistor 10 during heating is sensed at step S30. At this time, the potential difference $V_C$ across the ends of the thermistor 10 employed in Eq. (3) is obtained simultaneously. Next, at step S31, the blood flow velocity v is computed by the blood flow velocity arithmetic means 32 in accordance with Eq. (3), and the result is outputted to the continuous cardiac output arithmetic means 33. The parameter s representing the blood vessel sectional area is obtained by the continuous cardiac output arithmetic means 33 in accordance with Eq. (4), and the parameter is stored in the register S at step S32.

FIG. 8 is a flowchart illustrating the details of a continuous cardiac output measurement routine of the embodiment. The thermistor 10 is heated at the constant current $I_C$ at step S41, blood temperature $T_P$ is measured at step S42, and the equilibrum temperature $T_C$ of the thermistor 10, which is being heated, is measured at step S43. The potential $V_C$ across the thermistor 10 is obtained at the same time. The blood flow velocity v is calculated at step S44 by the blood flow velocity arithmetic means 32 in accordance with the Eq. (3), and v is outputted to the continuous cardiac output arithmetic means 33. Next, at step S45, the continuous cardiac output arithmetic means 33 multiplies the parameter s by the blood flow velocity v to obtain the continuous cardiac output $C_o'$. The continuous cardiac output $C_o'$ obtained is displayed at step S46.

Though the foregoing embodiment has been described with regard to a cardiac output measurement apparatus, the invention is not limited thereto. The invention is applicable also to various other measuring devices such as electronic clinical thermometers, sphygmomanometers, electrocardiographs, heart rate meters and electroencephalographs.

The foregoing embodiment relates to a temperature sensor probe circuit using a temperature-sensitive element (thermistor). However, the invention is not limited thereto, for it is possible to apply the invention to probe circuits using various sensors, such as a variety of electrodes, ion sensors, pressure sensors and optical sensors.

Though the embodiment has been described with regard to a case where a DC bias (constant current and constant voltage) is applied to a probe circuit, the invention is not limited thereto but is usable also in cases where an AC bias or pulse signal is applied. It will suffice to compare AC bias leakage currents using effective values, and it will suffice to compare pulse signal leakage currents in a predetermined interval.

In accordance with the present invention as described above, the engage of signals between the biological information sensing circuit and the biological information processing circuit is performed in an electrically isolated state. As a result, the isolation of the measurement section including the probe circuit is greatly improved, and the structure is such that leaks from the outside can be prevented with much greater ease.

In accordance with the present invention, a first power supply circuit for supplying power solely to the biological information sensing circuit is provided, and supply of power from a second power supply circuit to the first power supply circuit is carried out in an electrically isolated state. This means that the biological information sensing circuit can be electrically cut off from the AC power supply and the power supply circuit section of the apparatus main body with greater reliability, thus making safe measurement possible.

In accordance with the present invention, whether or not leakage current is present in a living body is sensed by sensing and comparing a value corresponding to a current value applied to a sensing element and a value corresponding to a current value fed back to the bias circuit via the sensing element. As a result, very small leakage currents can be detected so that it is possible to take safety measures immediately.

In accordance with the present invention, a predetermined bias is applied solely to a corrective element in the probe, and the amount of electricity read from the corrective element is compared with a predetermined value to identify the type of probe connected. This makes it possible to accurately read the characteristics of a variance in sensing means characteristics so that the type of sensing means can be automatically identified in accurate fashion.

What is claimed is:

1. A biological information measurement apparatus, comprising:
   biological information detecting means, coupled to a patient, including means for electrically detecting biological information of the patient, means for generating a feedback current from a predetermined current and means for supplying an analog signal indicative of biological information;
   galvanizing means, electrically coupled to said biological information detecting means, for supplying said biological information detecting means with the predetermined current;
   A/D transform means, coupled to said biological information detecting means, for transforming the analog signal to a digital signal;
   at least one photodiode means for converting the digital signal to a light signal;

at least one optical fiber, optically coupled to said photodiode means, for transmitting the light signal;

at least one phototransistor means, optically coupled to said optical fiber, for converting the light signal to an electrical signal;

biological information processing means, electrically coupled to said phototransistor means, for digitally processing the biological information based on the electrical signal;

first power supply means for supplying electric power to said biological information processing means;

second power supply means, supplied with electric power from said first power supply means, for supplying electric power, electrically isolated from said first power supply means, to said A/D transform means and said galvanizing means;

current control means for selectively cutting off the electric power supplied by said second power supply means to said biological information detecting means via said galvanizing means, including current detecting means for detecting a difference between the predetermined current supplied by said galvanizing means to said biological information detecting means and the feedback current from said biological information detecting means and current cutoff means for cutting off the current from said galvanizing means to said biological information detecting means, when the current detected by said current detecting means is larger than a predetermined value; and display means for displaying the biological information processed by said biological processing means.

2. The biological information measurement apparatus according to claim 1, further comprising power transmission means, having a primary winding circuit connected to said first power supply means and a secondary winding circuit connected to said second power supply means, for transmitting the electric power from said first power supply means to said second power supply means.

3. A biological information measurement apparatus utilizing a catheter, comprising:

detecting means, including at least one sensor in the catheter, for electrically detecting biological data provided by said sensor and for outputting a detection signal indicative of the biological information;

control means, including means for receiving the detection signal at a remote location means, means for generating a control signal to control operation of said detecting means and means for processing the detection signal to produce biological information;

optical data transmitting means, coupled to said detecting mean sand said control means, for transmitting the detection signal and the control signal as light signals between said detecting means and said control means;

first power supply means for supplying electric power to said control means;

second power supply means, supplied with the electric power from said first power supply means, for supplying electric power to said detecting means, including supplying a first current to said sensor;

means for detecting a second current flowing through said sensor;

comparing means for detecting a difference between the first and second currents and for comparing the difference with a predetermined value; and current cutoff means, interposed between said second power supply means and said sensor, for selectively cutting off the first current supplied to said sensor from said second power supply means when the difference detected by said comparing means is greater than the predetermined value.

* * * * *